United States Patent [19]

Hicks, Jr.

[11] Patent Number: 6,072,104
[45] Date of Patent: Jun. 6, 2000

[54] SOYBEAN VARIETY 9594

[75] Inventor: John Dudley Hicks, Jr., Greenville, Miss.

[73] Assignee: Pioneer Hi-Bred International, Inc., Des Moines, Iowa

[21] Appl. No.: 08/783,027

[22] Filed: Jan. 14, 1997

[51] Int. Cl.$^7$ .............................. A01H 5/00; A01H 5/10; A01H 1/02; C12N 5/04
[52] U.S. Cl. ........................ 800/312; 800/260; 435/415
[58] Field of Search .................................. 800/200, 255, 800/DIG. 26, 312, 260; 435/415; 47/58, DIG. 1

[56] References Cited

U.S. PATENT DOCUMENTS 5,534,425  7/1996  Fehr et al. ........................... 435/172.1

OTHER PUBLICATIONS

Jaycox, "Ecological Relationships between Honey Bees and Soybeans," *American Bee Journal* vol. 110(8): 306–307 (Aug. 1970).

Komatsuda, T. et al., Maturation and Germination of Somatic Embryos as Affected by Sucrose and Plant Growth Regulators in Soybeans Glycine gracilis Skvortz and Glycine max (L.) Merr., *Plant Cell. Tissue and Organ Culture,* 28:103–113, 1992.

Dhir, S. et al., "Regeneration of Fertile Plants from Protoplasts of Soybean (Glycine max L. Merr.): Genotypic Differences in Culture Response," *Plant Cell Reports* (1992) 11:285–289.

Pandey, P. et al., "Plant Regeneration from Leaf and Hypocotyl Explants of Glycine wightii (W. and A.) VERDC. var longicauda," *Japan J. Breed.* 42:1–5 (1992).

Shetty, K., et al., "Stimulation of In Vitro Shoot Organogenesis in Glycine max (Merrill.) by Allantoin and Amides," Plant Science 81:(1992) 245–251.

Stephens, P.A. et al., "Agronomic Evaluation of Tissue–Culture–Derived Soybean Plants," *Theor. Appl. Genet.* (1991) 82:633–635.

Komatsuda, T. et al., "Genotype X Sucrose Interactions for Somatic Embryogenesis in Soybean," *Crop Sci.* 31:333–337 (1991).

"Economic Implications of Modified Soybean Traits Summary Report", Iowa Soybean Promotion Board & American Soybean Association Special Report 92S, May 1990.

Caldwell, B. E. ed. 1973. "Soybeans: Improvement, Production, and Uses" Amer. Soc. Agron. Monograph No. 16.

Buttery, B. R., and R. I. Buzzell 1968. "Peroxidase Activity in Seed of Soybean Varieties" Crop Sci. 8: 722–725.

Hymowitz, T. 1973. "Electrophoretic analysis of SBTI–A2 in the USDA Soybean Germplasm Collection" Crop Sci., 13: 420–421.

Payne R. C., and L.F. Morris, 1976. "Differentiation of Soybean Cultivars by Seedling Pigmentation Patterns" J. Seed. Technol. 1: 1–19.

Graef et al (1994) Crop Sci 34:818, 'Coffax' Soybean.

Leffel, R.C. (1992) Crop Sci. 32:502, 'BARC–8' Soybean.

Allen et al (1986) Crop Sci: 26:649, 'TNS–85' Soybean.

Buss et al (1988) Crop Sci 28:1024–1025, 'Hutcheson' Soybean.

*Primary Examiner*—Elizabeth F. McElwain
*Attorney, Agent, or Firm*—Pioneer Hi-Bred International, Inc.

[57] ABSTRACT

A soybean variety designated 9594, the plants and seeds of soybean variety 9594, methods for producing a soybean plant produced by crossing the variety 9594 with itself or with another soybean plant, and hybrid soybean seeds and plants produced by crossing the variety 9594 with another soybean line or plant.

14 Claims, No Drawings

SOYBEAN VARIETY 9594

FIELD OF THE INVENTION

This invention is in the field of soybean breeding, specifically relating to a soybean variety designated 9594.

BACKGROUND OF THE INVENTION

The present invention relates to a new and distinctive soybean variety, designated 9594 which has been the result of years of careful breeding and selection. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, and better agronomic qualities.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Soybean plants (i.e. Glycine Max) are recognized to be naturally self-pollinated plants which, while capable of undergoing cross-pollination, rarely do so in nature. Insects are reported by some researchers to carry pollen from one soybean plant to another and it generally is estimated that less than one percent of soybean seed formed in an open planting can be traced to cross-pollination, i.e. less than one percent of soybean seed formed in an open planting is capable of producing $F_1$ hybrid soybean plants, See Jaycox, "Ecological Relationships between Honey Bees and Soybeans," appearing in the American Bee Journal Vol. 110(8): 306–307 (August 1970). Thus intervention for control of pollination is critical to establishment of superior varieties.

A cross between two different homozygous lines produces a uniform population of hybrid plants that may be heterozygous for many gene loci. A cross of two plants each heterozygous at a number of gene loci will produce a population of hybrid plants that differ genetically and will not be uniform. Regardless of parentage, plants that have been self-pollinated and selected for type for many generations become homozygous at almost all gene loci and produce a uniform population of true breeding progeny.

Soybeans (Glycine max.), can be bred by both self-pollination and cross-pollination techniques. Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Pedigree breeding is commonly used for the improvement of self-pollinating crops. Two parents that possess favorable, complementary traits are crossed to produce an $F_1$. An $F_2$ population is produced by selfing one or several $F_1$'s or by intercrossing two $F_1$'s (sib mating). Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Backcross breeding has been used to transfer genes for simply inherited, highly heritable traits into a desirable homozygous variety or inbred line that is utilized as the recurrent parent. The source of the traits to be transferred is called the donor parent. The resulting plant is expected to have the attributes of the recurrent parent (e.g., variety) and the desirable traits transferred from the donor parent. After the initial cross, individuals possessing the desired traits of the donor parent are selected and repeatedly crossed (backcrossed) to the recurrent parent. The resulting plant is expected to have the attributes of the recurrent parent (e.g., variety) and the desirable traits transferred from the donor parent. This approach has been used extensively for breeding disease resistant varieties.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial varieties; those still deficient in a few traits may be used as parents to produce new populations for further selection.

These processes, which lead to the final step of marketing and distribution, can take from eight to twelve years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. Generally a single observation is inconclusive, so replicated observations are required to provide a better estimate of its genetic worth.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents, as the breeder is unable to direct how the genomes combine or how they will interact with the environmental conditions. This unpredictability results in the expenditure of large amounts of research resources in the development of a superior new soybean inbred line.

The goal of soybean breeding is to develop new, unique and superior soybean varieties. In practical application of a chosen breeding program, the breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made during and at the end of the growing season. The varieties which are developed are unpredictable for the reasons already mentioned.

Mass and recurrent selections can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

Soybean, Glycine max (L), is an important and valuable field crop. Thus, a continuing goal of soybean breeders is to develop stable, high yielding soybean varieties that are agronomically sound. The reasons for this goal are obviously to maximize the amount of grain produced on the land used and to supply food for both animals and humans. To accomplish this goal, the soybean breeder must select and develop soybean plants that have the traits that result in superior varieties.

Pioneer soybean research staff create over 500,000 new inbreds each year. Of those new inbreds, less than 50 and more commonly less than 25 are actually selected for commercial use.

SUMMARY OF THE INVENTION

According to the invention, there is provided a novel soybean variety, designated 9594. This invention thus relates to the seeds of soybean variety 9594, to the plants of soybean variety 9594 and to methods for producing a soybean plant produced by crossing soybean variety 9594 with itself or another soybean plant, and the creation of variants by mutagenesis or transformation of soybean variety 9594.

Definitions

In the description and tables which follow, a number of terms are used. In order to provide a clear and consistent understanding of the specification and claims, including the scope to be given such terms, the following definitions are provided:

B/A=BUSHELS PER ACRE. The seed yield in bushels/acre is the actual yield of the grain at harvest.

BSR=BROWN STEM ROT TOLERANCE. This is a visual disease score from 1 to 9 comparing all genotypes in a given test. The score is based on leaf symptoms of yellowing and necrosis caused by brown stem rot. A score of 9 indicates no symptoms. Visual scores range down to a score of 1 which indicates severe symptoms of leaf yellowing and necrosis.

CNKR=STEM CANKER TOLERANCE. This is a visual disease score from 1 to 9 comparing all genotypes in a given test. The score is based upon premature plant death. A score of 9 indicates no symptoms, whereas a score of 1 indicates the entire experimental unit died very early.

COTYLEDON. A cotyledon is a type of seed leaf. The cotyledon contains the food storage tissues of the seed.

EMBRYO. The embryo is the small plant contained within a mature seed.

$F_3$. This symbol denotes a generation resulting from the selfing of the $F_2$ generation along with selection for type and rogueing of off-types. The "F" number is a term commonly used in genetics, and designates the number of the filial generation. The "$F_3$" generation denotes the offspring resulting from the selfing or self mating of members of the generation having the next lower "F" number, viz. the $F_2$ generation.

FECL=IRON-DEFICIENCY CHLOROSIS. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves.

FEY=Frogeye Tolerance. This is a visual disease score from 1 to 9 comparing all genotypes in a given test. The score is based upon leaf lesions. A score of 9 indicates no lesions, whereas a score of 1 indicates severe leaf necrosis.

HABIT. This refers to the physical appearance of a plant. It can be either determinate or indeterminate. In soybeans indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are these in which stem growth ceases at flowering time. Most flowers develop simultaneously, and most pods fill at approximately the same time.

HGT=Plant Height. Plant height is taken from the top of soil to top pod of the plant and is measured in inches.

HILUM. This refers to the scar left on the seed which marks the place where the seed was attached to the pod prior to it (the seed) being harvested.

HYPL=HYPOCOTYL ELONGATION. This score indicates the ability of the seed to emerge when planted 3" deep in sand and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

HYPOCOTYL. A hypocotyl is the portion of an embryo or seedling between the cotyledons and the root. Therefore, it can be considered a transition zone between shoot and root.

LDG=LODGING RESISTANCE. Lodging is rated on a scale of 1 to 9. A score of 9 indicates erect plants. A score of 5 indicates plants are leaning at a 45° angle in relation to the ground and a score of 1 indicates plants are laying on the ground.

LEAFLETS. These are part of the plant shoot, and they manufacture food for the plant by the process of photosynthesis.

LLE=Linoleic Acid Percent. Linoleic acid is one of the five most abundant fatty acids in soybeans seeds. It is measured by gas chromatography and is reported as a percent of the total oil content.

LLN=Linolenic Acid Percent. Linolenic acid is one of the five most abundant fatty acids in soybeans seeds. It is measured by gas chromatography and is reported as a percent of the total oil content.

MAT ABS=ABSOLUTE MATURITY. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP. This refers to an agreed-on industry division of groups of varieties, based on the zones in which they are adapted primarily according to day length or latitude. They consist of very long day length varieties (Groups 000, 00, 0), and extend to very short day length varieties (Groups VII, VIII, IX, X).

OIL=Oil Percent. Soybean seeds contain a considerable amount of oil. Oil is measured by NIR spectrophotometry, and is reported on an as is percentage basis.

OLC=OLEIC ACID PERCENT. Oleic acid is one of the five most abundant fatty acids in soybean seeds. It is measured by gas chromatography and is reported as a percent of the total oil content.

PLM=Palmitic Acid Percent. Palmitic acid is one of the five most abundant fatty acids in soybean seeds. It is measured by gas chromotography and is reported as a percent of the total oil content.

POD. This refers to the fruit of a soybean plant. It consists of the hull or shell (pericarp) and the soybean seeds.

PRT=PHYTOPHTHORA TOLERANCE. Tolerance to Phytophthora root rot is rated on a scale of 1 to 9, with a score of 9 being the best or highest tolerance ranging down to a score of 1 which indicates the plants have no tolerance to Phytophthora.

PRM=Predicted Relative Maturity. Soybean maturities are divided into relative maturity groups. In the United States the most common maturity groups are 0 through VIII. Within these maturity groups the industry generally divides maturities into tenths of a relative maturity group. Within narrow comparisons, the difference of a tenth of a relative maturity group equates very roughly to a day difference in maturity at harvest.

PRO=Protein Percent. Soybean seeds contain a considerable amount of protein. Protein is generally measured by NIR spectrophotometry, and is reported on an as is percentage basis.

PUBESCENCE. This refers to a covering of very fine hairs closely arranged on the leaves, stems and pods of the soybean plant.

S/LB=Seeds per Pound. Soybean seeds vary in seed size, therefore, the number of seeds required to make up one pound also varies. This affects the pounds of seed required to plant a given area, and can also impact end uses.

SH=SHATTERING. This refers to the amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

SHOOTS. These are a portion of the body of the plant. They consist of stems, petioles and leaves.

STC=STEARIC ACID PERCENT. Stearic acid is one of the five most abundant fatty acids in soybeans seeds. It is measured by gas chromatography and is reported as a percent of the total oil content.

WH MD=WHITE MOLD TOLERANCE. This is a visual disease score from 1 to 9 comparing all genotypes in a given test. The score is based upon observations of mycelial growth and death of plants. A score of 9 indicates no symptoms. Visual scores of 1 indicate complete death of the experimental unit.

DETAILED DESCRIPTION OF THE INVENTION

A soybean variety needs to be highly homogeneous, homozygous and reproducible to be useful as a commercial variety. There are many analytical methods available to determine the homozygotic and phenotypic stability of these varieties.

The oldest and most traditional method of analysis is the observation of phenotypic traits. The data is usually collected in field experiments over the life of the soybean plants to be examined. Phenotypic characteristics most often observed are for traits associated with seed yield, seed protein and oil content, lodging resistance, disease resistance, maturity, plant height, and shattering.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The variety of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in 9594, as described in Table 1 (Variety Description Information).

Soybean variety 9594 is a white flowered soybean variety with gray pubescence and buff hila. The variety has good stems and roots. Soybean variety 9594 exhibits exceptional yield for its maturity. The variety demonstrates moderate resistance to Southern Root-Knot Nematode and Stem Canker. The variety is specifically adapted for the South Central United States and Southeast coast. It performs well in tight clay soils, narrow rows and most high yield environments.

Soybean variety 9594, being substantially homozygous, can be reproduced by planting seeds of the line, growing the resulting soybean plants under self-pollinating or sib-pollinating conditions, and harvesting the resulting seed, using techniques familiar to the agricultural arts.

TABLE 1

VARIETY DESCRIPTION INFORMATION
9594

| | |
|---|---|
| A. | Mature Seed Characteristics: |
| | Seed Shape: spherical flattened |
| | Seed Coat Color: yellow |
| | Seed Coat Luster: dull |
| | Seed Size (grams per 100 seeds): 16 |

TABLE 1-continued

VARIETY DESCRIPTION INFORMATION
9594

| | |
|---|---|
| | Hilum Color: buff |
| | Cotyledon Color: yellow |
| | Seed Protein Peroxidase Activity: low |
| | Hypocotyl Color: green only |
| B. | Leaf: |
| | Leaflet Shape: ovate |
| | Leaflet Size: medium |
| C. | Plant Characteristics: |
| | Flower Color: white |
| | Pod Color: tan |
| | Plant Pubescence Color: gray |
| | Plant Types: intermediate |
| | Plant Habit: Determinate |
| | Maturity Group: V |
| D. | Bacterial Diseases (S = susceptible R = resistant) |
| | Bacterial Pustule (*Xanthomonas phaseoli* var. Sojensis): R |
| | Bacterial Blight (*Pseudomonas glycinea*): S |
| | Wildfire (*Pseudomonas tabaci*): R |
| E. | Fungal Diseases (S = susceptible R = resistant) |
| | Brown Spot (*Septoria glycines*): S |
| | Brown Stem Rot (*Cephalosporium gregatum*): S |
| | Pod and Stem Blight (*Diaporthe phaseolorum* var. *sojae*): S |
| | Purple Seed Stain (*Cercospora kikuchii*): S |
| | Rhizoctonia Root Rot (*Rhizoctonia solani*): S |
| | Phytophthora Rot (*Phytophthora megasperma* var. *sojae*): |
| | Race 1: S    Race 2: S    Race 3: S    Race 5: S |
| | Race 7: S    Race 8: S    Race 9: S |
| F. | Viral Diseases (S = susceptible R = resistant) |
| | Bud Blight (Tobacco Ringspot Virus): S |
| | Yellow Mosaic (Bean Yellow Mosaic Virus): S |
| | Cowpea Mosaic (Cowpea Chlorotic Virus): S |
| G. | Nematode Diseases (S = susceptible R = resistant) |
| | Soybean Cyst Nematode |
| | Race 3: S |
| | Southern Root Knot Nematode: moderately R |
| H. | Physiological Responses (S = susceptible R = resistant) |
| | Iron Chlorosis on Calcareous Soil: Not tested |

(PVP Certificate No.) is a Pioneer Hi-Bred International, Inc. proprietary variety.

Publications useful as references in interpreting Table 1 include:

Caldwell, B. E. ed. 1973. "Soybeans: Improvement, Production, and Uses" Amer. Soc. Agron. Monograph No. 16;

Buttery, B. R., and R. I. Buzzell 1968. "Peroxidase Activity in Seed of Soybean Varieties" Crop Sci. 8: 722–725;

Hymowitz, T. 1973. "Electrophoretic analysis of SBTI-A2 in the USDA Soybean Germplasm Collection" Crop Sci., 13: 420–421;

Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

Industrial Applicability

This invention also is directed to methods for producing a soybean plant by crossing a first parent soybean plant with a second parent soybean plant wherein the first or second parent soybean plant is a soybean plant of the variety 9594. Further, both first and second parent soybean plants can come from the soybean variety 9594. Thus, any such methods using the soybean variety 9594 are part of this invention: selfing, backcrosses, hybrid production, crosses to populations, and the like. All plants produced using soybean variety 9594 as a parent are within the scope of this invention. Advantageously, the soybean variety could be used in crosses with other, different, soybean plants to produce first generation ($F_1$) soybean hybrid seeds and plants with superior characteristics. The variety of the invention can also be used for transformation where exogenous genes are introduced and expressed by the variety of the invention. Genetic variants created either through traditional breeding methods using variety 9594 or through transformation of 9594 by any of a number of protocols known to those of skill in the art are intended to be within the scope of this invention.

Production of a genetically modified plant tissue by transformation combines teachings of the present disclosure with a variety of techniques and expedients known in the art. In most instances alternate expedients exist for each stage of the overall process. The choice of expedients depends on the variables such as the plasmid vector system chosen for the cloning and introduction of the desired recombinant DNA molecule, as well as the particular structural gene, promoter elements and upstream elements used. Persons skilled in the art are able to select and use appropriate alternatives to achieve functionality. Culture conditions for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition Sprague et al. (Eds. pp. 345–387) American Society of Agronomy Inc. et al. 1988. Methods of introducing expression vectors into plant tissue include the direct infection or co-cultivation of plant cells with *Agrobacterium tumefaciens*, Horsch et al., Science, 227: 1229 (1985). Descriptions of Agrobacterium vector systems and methods for Agrobacterium-mediated gene transfer provided by Gruber, et al. supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device. Transformant plants obtained with the protoplasm of the invention are intended to be within the scope of this invention.

As used herein, the term plant includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, silk and the like.

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," *Crop Sci.* 31: 333–337 (1991); Stephens, P. A. et al., "Agronomic Evaluation of Tissue-Culture-Derived Soybean Plants," *Theor. Appl. Genet.* (1991) 82: 633–635; Komatsuda, T. et al., "Maturation and Germination of Somatic Embryos as Affected by Sucrose and Plant Growth Regulators in Soybeans Glycine gracilis Skvortz and Glycine max (L.) Merr.," *Plant Cell, Tissue and Organ Culture,* 28: 103–113 (1992); Dhir, S. et al., "Regeneration of Fertile Plants from Protoplasts of Soybean (Glycine max L. Merr.): Genotypic Differences in Culture Response," *Plant Cell Reports* (1992) 11: 285–289; Pandey, P. et al., "Plant Regeneration from Leaf and Hypocotyl Explants of Glycine wightii (W. and A.) VERDC. var longicauda," *Japan J. Breed.* 42: 1–5 (1992); and Shetty, K., et al., "Stimulation of In Vitro Shoot Organogenesis in Glycine max (Merrill.) by Allantoin and Amides," Plant Science 81: (1992) 245–251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of variety 9594.

The seed of soybean variety 9594, the plant produced from the inbred seed, the hybrid soybean plant produced from the crossing of the inbred, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990. Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

PERFORMANCE EXAMPLES OF 9594

In the examples that follow, the traits and characteristics of soybean variety 9594 are given. The data collected on inbred soybean variety 9594 is presented for the key characteristics and traits.

Table 2A is a paired comparison report comparing variety 9594 with similarly adapted variety 9583. According to the Table, variety 9594 demonstrates significantly higher yield and is significantly taller than variety 9583. Variety 9594 is later maturing with significantly higher predicted relative maturity and absolute maturity scores.

Table 2B compares variety 9594 with another similarly adapted variety 9584. The results indicate that variety 9594 is significantly higher yielding than variety 9584. Variety 9594 is significantly later to mature and is taller than variety 9584. Variety 9594 also exhibits a slightly lower seed protein and higher seed oil content, compared to variety 9584.

Table 2C compares variety 9594 with another similarly adapted variety, 9592. As can be seen from the table variety 9594 is significantly higher yielding and is significantly earlier maturing with significantly lower predicted relative maturity and absolute maturity scores than 9592. Variety 9594 exhibits significantly shorter stature with slightly higher resistance to root lodging than variety 9592. Variety 9594 also demonstrates a significantly lower seed protein content compared to seed from variety 9592.

Table 2D compares variety 9594 to yet another similarly adapted variety, 9593. The results show that variety 9594 is significantly higher yielding than variety 9593. Variety 9594 exhibits significantly shorter plant stature and matures significantly later than variety 9593.

Table 2E compares soybean variety 9594 with a similarly adapted variety, 9611. The results indicate that variety 9594 is significantly higher yielding than variety 9611. Variety 9594 is significantly shorter and matures significantly earlier than variety 9611. Variety 9594 exhibits a significantly lower seed protein and higher seed oil content than variety 9611.

TABLE 2A

PAIRED COMPARISON REPORT
VARIETY #1 = 9594
VARIETY #2 = 9583

|  |  | B/A | MAT | PRM | HGT | LDG |
|---|---|---|---|---|---|---|
| TOTAL SUM | 1 | 58.9 | 136.0 | 59 | 32.0 | 5.1 |
|  | 2 | 50.2 | 132.2 | 57 | 25.6 | 7.2 |
|  | LOCS | 22 | 8 | 4 | 10 | 12 |
|  | DIFF | 8.7 | 3.8 | 2 | 6.5 | 2.1 |
|  | PR > T | .000# | .012+ | .017+ | .000# | .000# |

*= significant at the 10% level
+= significant at the 5% level
= significant at the 1% level

TABLE 2B

PAIRED COMPARISON REPORT
VARIETY#1 = 9594
VARIETY#2 = 9584

|  | B/A | MAT | PRM | HGT | LDG | PRO | OIL | FEY |
|---|---|---|---|---|---|---|---|---|
| TOTAL SUM |  |  |  |  |  |  |  |  |
| 1 | 58.0 | 136.3 | 59 | 32.0 | 5.5 | 42.2 | 21.6 | 5.7 |
| 2 | 50.4 | 132.7 | 57 | 31.2 | 5.8 | 43.1 | 21.3 | 8.3 |
| LOCS | 70 | 28 | 12 | 46 | 48 | 4 | 4 | 1 |

TABLE 2B-continued

PAIRED COMPARISON REPORT
VARIETY#1 = 9594
VARIETY#2 = 9584

|  | B/A | MAT | PRM | HGT | LDG | PRO | OIL | FEY |
|---|---|---|---|---|---|---|---|---|
| DIFF | 7.7 | 3.7 | 2 | 0.8 | 0.4 | 0.9 | 0.3 | 2.7 |
| PR > T | .000# | .000# | .000# | 0.108 | .000# | 0.119 | 0.109 |  |

*= significant at the 10% level
+= significant at the 5% level
= significant at the 1% level

TABLE 2C

PAIRED COMPARISON REPORT
VARIETY#1 = 9594
VARIETY#2 = 9592

|  | B/A | MAT | PRM | HGT | LDG | PRO | OIL | FEY |
|---|---|---|---|---|---|---|---|---|
| TOTAL SUM |  |  |  |  |  |  |  |  |
| 1 | 57.9 | 136.7 | 59 | 32.2 | 5.6 | 42.2 | 21.6 | 5.7 |
| 2 | 49.4 | 137.6 | 60 | 36.9 | 5.4 | 44.1 | 21.8 | 8.0 |
| LOCS | 53 | 21 | 9 | 35 | 37 | 4 | 4 | 1 |
| DIFF | 8.5 | 0.9 | 1 | 4.7 | 0.1 | 1.9 | 0.2 | 2.3 |
| PR > T | .000# | .001# | .007# | .000# | 0.446 | .024+ | 0.161 |  |

*= significant at the 10% level
+= significant at the 5% level
= significant at the 1% level

TABLE 2D

PAIRED COMPARISON REPORT
VARIETY #1 = 9594
VARIETY #2 = 9593

|  | B/A | MAT | PRM | HGT | LDG | PRO | OIL | FEY |
|---|---|---|---|---|---|---|---|---|
| TOTAL SUM |  |  |  |  |  |  |  |  |
| 1 | 57.9 | 136.7 | 59 | 32.2 | 5.6 | 42.2 | 21.6 | 5.7 |
| 2 | 48.3 | 135.6 | 58 | 35.2 | 5.5 | 43.4 | 21.3 | 8.0 |
| LOCS | 53 | 21 | 9 | 35 | 37 | 4 | 4 | 1 |
| DIFF | 9.7 | 1.2 | 1 | 3 | 0.1 | 1.2 | 0.4 | 2.3 |
| PR > T | .000# | .000# | .011+ | .000# | 0.459 | 0.113 | 0.521 |  |

*= significant at the 10% level
+= significant at the 5% level
= significant at the 1% level

TABLE 2E

PAIRED COMPARISON REPORT
VARIETY#1 = 9594
VARIETY#2 = 9611

|  | B/A | MAT | PRM | HGT | LDG | PRO | OIL | FEY |
|---|---|---|---|---|---|---|---|---|
| TOTAL SUM |  |  |  |  |  |  |  |  |
| 1 | 57.9 | 136.7 | 59 | 32.2 | 5.6 | 42.2 | 21.6 | 5.7 |
| 2 | 52.3 | 138.0 | 60 | 34.6 | 5.7 | 44.2 | 20.7 | 7.0 |
| LOCS | 53 | 21 | 9 | 35 | 37 | 4 | 4 | 1 |
| DIFF | 5.6 | 1.2 | 1 | 2.4 | 0.1 | 1.9 | 1 | 1.3 |
| PR > T | .000# | .000# | .006# | .000# | 0.252 | .014+ | .063* |  |

*= significant at the 10% level
+= significant at the 5% level
= significant at the 1% level Deposits Applicant has made a deposit of at least 2500 seeds of Soybean Variety 9594 with the American Type Culture Collection (ATCC), Manassas, Va. 20110 USA, ATCC Deposit No. 209764. The seeds deposited with the ATCC on Apr. 10, 1998 were taken from the deposit maintained by Pioneer Hi-Bred International, Inc., 800 Capital Square, 400 Locust Street, Des Moines, Iowa 50309-2340 since prior to the filing date of this application. This deposit of the Soybean Variety 9594 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.). U.S. Plant Variety Protection of Soybean Variety 9594 has been applied for under Application No. 9,600,377.

What is claimed is:

1. A soybean seed designated 9594, representative seed of said soybean 9594 having been deposited under ATCC Accession No. 209764.

2. A soybean plant, or its parts, grown from the seed of claim 1, representative seed having been deposited under ATCC Accession No. 209764.

3. Pollen of the plant of claim 2.

4. An ovule of the plant of claim 2.

5. A soybean plant, and parts thereof, having all the physiological and morphological characteristics of the plant of claim 2.

6. A tissue culture of regenerable cells of the plant of claim 2.

7. A tissue culture according to claim 6, the cells or protoplasts being of a tissue selected from the group consisting of: leaves, pollen, embryos, roots, pods, flowers, and stalks.

8. A soybean plant regenerated from the tissue culture of claim 6, capable of expressing all the morphological and physiological characteristics of variety 9594, representative seed of said variety 9594 having been deposited under ATCC Accession No. 209764.

9. A soybean plant with all of the physiological and morphological characteristics of the soybean plant of claim 2, said soybean plant produced by the tissue culture process using soybean plant of claim 2 as the starting material for such a process.

10. A method for producing a first generation ($F_1$) hybrid soybean seed comprising crossing the plant of claim 2 with a different inbred parent soybean plant and harvesting the resultant first generation ($F_1$) hybrid soybean seed.

11. A method for producing a first generation ($F_1$) hybrid soybean seed comprising:

crossing the plant of claim 2 with a different inbred parent soybean plant and harvesting the resultant first generation ($F_1$) hybrid soybean seed wherein the inbred soybean plant of claim 2 is the female parent.

12. A method for producing a first generation ($F_1$) hybrid soybean seed comprising crossing the plant of claim 2 with a different inbred parent soybean plant and harvesting the resultant first generation ($F_1$) hybrid soybean seed wherein the inbred soybean plant of claim 2 is the male parent.

13. An $F_1$ hybrid soybean seed produced by crossing the plant of claim 2 with a different parent soybean plant.

14. An $F_1$ hybrid soybean plant, or plants thereof, grown from the seeds of claim 13.

* * * * *

UNITED STATES PATENT AND TRADEMARK OFFICE
CERTIFICATE OF CORRECTION

PATENT NO.    : 6,072,104
DATED         : June 6, 2000
INVENTOR(S)   : John Dudley Hicks, Jr.

It is certified that error appears in the above-identified patent and that said Letters Patent is hereby corrected as shown below:

Column 13,
Between the lines 22 and 23 insert the following:
-- The foregoing invention has been described in detail by way of illustration and example for purposes of clarity and understanding. However, it will be obvious that certain changes and modifications such as single gene modifications and mutations, somoclonal variants, variant individuals selected from the large populations of the plants of the instant inbred and the like may be practiced within the scope of the invention, as limited only by the scope of the appended claims. --

Signed and Sealed this

Twenty-seventh Day of November, 2001

Attest:

NICHOLAS P. GODICI
Attesting Officer    Acting Director of the United States Patent and Trademark Office